United States Patent
Merchant et al.

(10) Patent No.: US 9,707,329 B2
(45) Date of Patent: Jul. 18, 2017

(54) PROCESS FOR REGENERATION OF SPENT ZIRCONIUM PHOSPHATE FOR REUSE IN SORBENT TREATMENTS

(71) Applicant: Fresenius Medical Care Holdings, Inc., Waltham, MA (US)

(72) Inventors: Stephen A. Merchant, Oklahoma City, OK (US); Kerissa Adams, Norman, OK (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 266 days.

(21) Appl. No.: 14/060,761

(22) Filed: Oct. 23, 2013

(65) Prior Publication Data

US 2015/0108069 A1 Apr. 23, 2015

(51) Int. Cl.
*B01J 49/00* (2017.01)
*A61M 1/16* (2006.01)
(Continued)

(52) U.S. Cl.
CPC ............ *A61M 1/1696* (2013.01); *A61K 33/42* (2013.01); *B01J 20/0211* (2013.01); *B01J 20/0292* (2013.01); *B01J 20/28016* (2013.01); *B01J 20/3433* (2013.01); *B01J 20/3475* (2013.01); *B01J 49/53* (2017.01); *C01B 25/372* (2013.01); *B01J 2220/62* (2013.01)

(58) Field of Classification Search
CPC .. B01J 20/3433; B01J 20/3475; B01J 49/008; B01J 49/003; B01J 49/0069; B01J 49/0078; B01J 49/53

USPC .................................................. 210/670, 673
See application file for complete search history.

(56) References Cited

U.S. PATENT DOCUMENTS 2,571,271 A * 10/1951 Marks ................. B01J 49/0078
422/37
3,827,975 A * 8/1974 Bizot et al. ......... A61M 1/1696
210/195.2
(Continued)

FOREIGN PATENT DOCUMENTS

WO 2012047142 A1 4/2012

OTHER PUBLICATIONS

Pan et al, Selective heavy metals removal from waters by amorphous zirconium phosphate: Behavior and mechanism, Apr. 2007, Water Research, vol. 41 (2007), pp. 3103-3111.*
(Continued)

*Primary Examiner* — Matthew O Savage
(74) *Attorney, Agent, or Firm* — Kilyk & Bowersox, P.L.L.C.

(57) ABSTRACT

A method is provided for regenerating spent zirconium phosphate for reuse in sorbent dialysis treatments or other re-uses as a sorbent material. The method includes contacting spent zirconium phosphate with an aqueous disinfectant solution having at least one antimicrobial agent, and treating the resulting disinfected zirconium phosphate with an acidic solution to provide a treated zirconium phosphate that can be re-used as a sorbent material. Sorbent cartridge products containing the regenerated spent zirconium phosphate are also provided. Methods and systems for sorbent dialysis which re-use the regenerated zirconium phosphate such as part of sorbent cartridges, additionally are provided.

17 Claims, 5 Drawing Sheets

(51) Int. Cl.
    *C01B 25/37* (2006.01)
    *A61K 33/42* (2006.01)
    *B01J 20/34* (2006.01)
    *B01J 20/02* (2006.01)
    *B01J 20/28* (2006.01)
    *B01J 49/53* (2017.01)

(56) References Cited

U.S. PATENT DOCUMENTS

| | | | |
|---|---|---|---|
| 4,687,582 A * | 8/1987 | Dixon | B01J 47/02 |
| | | | 210/269 |
| 6,627,164 B1 * | 9/2003 | Wong | A61M 1/1696 |
| | | | 423/420.2 |
| 7,033,498 B2 * | 4/2006 | Wong | A61M 1/1696 |
| | | | 210/264 |
| 7,052,609 B2 | 5/2006 | Braunger et al. | |
| 8,173,566 B2 | 5/2012 | Olson et al. | |
| 8,187,991 B2 | 5/2012 | Osaheni et al. | |
| 2001/0008617 A1 | 7/2001 | Robles | |
| 2002/0112609 A1 | 8/2002 | Wong | |

OTHER PUBLICATIONS

International Search Report and Written Opinion issued in corresponding International Patent Application No. PCT/US2014/047919 dated Oct. 1, 2014 (12 pages).
Barhon et al., "Effect of Silver Activation of Zirconium Phosphate on the Methylene Blue Adsorption," Journal of Applied Sciences Research, vol. 5, No. 7, 2009, pp. 893-904.
Tan et al., "Antibacterial activity of silver-carried sodium zirconium phosphate prepared by ion-exchange reaction," Journal of the Ceramic Society of Japan, vol. 116, No. 6, 2008, pp. 767-770.

\* cited by examiner

PROCESS FOR REGENERATION OF SPENT ZIRCONIUM PHOSPHATE FOR REUSE IN SORBENT TREATMENTS

FIELD OF THE INVENTION

The present invention relates to methods for regenerating spent zirconium phosphate for re-use in sorbent treatments. The present invention further relates to sorbent cartridge products containing the regenerated spent zirconium phosphate, and also methods and systems for dialysis which use the sorbent cartridges.

BACKGROUND OF THE INVENTION

Zirconium phosphate (ZP) solid particles are used as ion-exchange materials and are particularly useful as a sorbent material in sorbent cartridges used for regeneration of dialysis solution. For instance, a sorbent cartridge containing ZP ion-exchange materials and other dialysate treatment components have been used for the REDY (REgenerative DialYsis) system. FIG. 1 shows various functions of each layer in a REDY cartridge, inclusive of zirconium phosphate. Among its functions, this commercial apparatus utilizes zirconium phosphate to remove the ammonia produced by the enzymatic decomposition of urea in the presence of urease contained in the cartridge. The regeneration efficiency of the zirconium phosphate, and hence the entire cartridge, typically decreases over time of use, for example, through deactivation by adsorbed ions, the presence or accumulation of materials that were not originally present in the layer, or other factors. It has been reported that the spent zirconium phosphate adsorbent is not regeneratable and must be discarded, such as indicated in U.S. Pat. No. 4,094,775. The used or spent zirconium phosphate is discarded and the entire sorbent cartridge may be replaced with a fresh cartridge to restore the function.

Methods for regeneration of sorbent materials have been proposed, for example, as shown in some published patent documents.

U.S. Pat. No. 7,052,609 relates to regeneration of adsorbent matrices that are used for the purification of substances from aqueous liquid samples derived from biological material. The method of the '609 patent is adapted to adsorbent matrices that are sensitive to hydrolysis either because of a sensitive base matrix or a sensitive ligand including also a sensitive spacer and is characterized in contacting at least one regeneration solution with the adsorbent matrix which comprises an organic solvent which is water-miscible and has a pH value ≤4, preferably ≤3 (acid solution) or ≥10 but <13 (alkaline solution).

U.S. Patent Application Publication No. 2001/0008617 relates to a process for recovering a metal from a metal-containing material, which uses sulfuric acid and/or an organic acid to regenerate spent sorbent from a metal recovery process. The process of the '617 published patent application relates generally to the regeneration of sorbents used for metal removal, and specifically to the regeneration of carbonaceous sorbents such as activated carbon.

U.S. Pat. No. 8,187,991 relates to a method of regenerating adsorbent material which includes providing a spent adsorbent material and contacting the adsorbent material with a solvent composition to facilitate removing oil and impurities from the spent solvent material.

U.S. Pat. No. 8,173,566 relates to a method and apparatus for regenerating a sorbent that has been poisoned by components derived from flue gas. In the method of the '566 patent, the sorbent is treated with an agent to remove the poisoning components and introduce a promoting agent into the sorbent.

WO 2012/047142 relates to a method for the removal of arsenic in a positive oxidation stage from an aqueous liquid. In the method of WO '142, an adsorbent that is used in the method that comprises a solid phase carrying a metal ion capable of binding arsenic is optionally regenerated and re-used.

The present investigators have recognized the need to improve the current sorbent dialysis technology and its accompanying treatment modalities. One such improvement is the regeneration or "recycle" of the spent sorbent material in the cartridge, such as for example, the zirconium phosphate. The investigators further have recognized that there is a need for sorbent cartridges for dialysis systems and/or other filtering systems that can effectively use such regenerated spent zirconium phosphate.

SUMMARY OF THE INVENTION

A feature of the present invention is a method to regenerate spent zirconium phosphate for reuse as a sorbent material.

A further feature of the present invention is a method to regenerate spent zirconium phosphate for reuse in sorbent-based dialysis treatments.

Another feature of the present invention is a sorbent cartridge comprising regenerated zirconium phosphate that is obtained from spent zirconium phosphate of a used sorbent cartridge.

A further feature of the present invention is a dialysis system comprising a dialyzer that uses dialysate to remove impurities from blood of a patient and at least one sorbent cartridge comprising regenerated spent zirconium phosphate for regenerating the dialysate.

An additional feature of the present invention relates to a method to regenerate or purify spent dialysis fluid comprising passing spent dialysis fluid through a sorbent cartridge comprising regenerated spent zirconium phosphate.

To achieve these and other advantages and in accordance with the purposes of the present invention, as embodied and broadly described herein, the present invention relates, in part, to a method for regeneration of spent zirconium phosphate comprising a) contacting spent zirconium phosphate with an aqueous disinfectant solution comprising an at least one antimicrobial agent to provide disinfected zirconium phosphate, and b) treating the disinfected zirconium phosphate with an acidic solution to provide a treated zirconium phosphate.

The present invention also relates to a method for regeneration of spent zirconium phosphate comprising a) contacting spent zirconium phosphate with an aqueous disinfectant solution comprising at least one antimicrobial agent (e.g., at least one halogen containing antimicrobial agent) to provide disinfected zirconium phosphate, b) filtering and washing the disinfected zirconium phosphate to provide washed disinfected zirconium phosphate with the washing providing a level of the antimicrobial agent in wash effluent of the washing of no greater than a first preselected value, c) treating the washed disinfected zirconium phosphate with an acidic solution to remove cations adsorbed thereon to provide a treated zirconium phosphate, d) filtering and washing the treated zirconium phosphate to provide washed treated zirconium phosphate with the washing providing a first total dissolved solids (TDS) level in wash effluent of the washing of no greater than a second preselected value, e) titrating the washed treated zirconium phosphate to a pH of about 5.5 to about 8.5 to provide titrated or neutralized zirconium phosphate, f) filtering and washing the titrated zirconium phosphate to provide washed titrated zirconium phosphate having a second total dissolved solids (TDS) level of no greater than a third preselected value, and g) drying the washed titrated zirconium phosphate to provide dried regenerated zirconium phosphate.

The present invention also relates to sorbent cartridges comprising the indicated treated zirconium phosphate.

The present invention also relates to a dialysis system comprising at least one dialyzer that uses dialysate to remove impurities from blood of a patient, and at least one of the indicated sorbent cartridges containing regenerated zirconium phosphate for regenerating and purifying the dialysate.

The present invention also relates to a method to regenerate or purify spent dialysis fluid comprising passing spent dialysis fluid through the indicated sorbent cartridge containing regenerated zirconium phosphate.

As used herein, "zirconium phosphate" or "ZP" can be represented by the molecular formula $Zr(HPO_4)_2 \cdot nH2O$. It will be appreciated that other representations of the material also may apply, such as with respect to its cation/hydrogen ion structures, such as those illustrated U.S. Pat. No. 7,033,498, which is incorporated in its entirety by reference herein.

As used herein, "spent zirconium phosphate" refers to zirconium phosphate that has been used as a sorbent material in a process wherein it becomes less active or efficient than the virgin ("fresh or unused") material.

As used herein, "control" or variant wording thereof refers to the reduction of the total level of at least one strain of microorganism present in spent zirconium phosphate to a desired level (even to undetectable limits).

As used herein, a "microorganism" can be bacterial, fungal, viral, individually or any combinations thereof.

As used herein, "antimicrobial" refers to the control of microorganisms such that the microorganism population is reduced, eliminated and/or prevented; "antibacterial" refers to control of bacteria such that the bacterial population is reduced, eliminated and/or prevented; "antifungal" refers to control of fungi such that the fungal population is reduced, eliminated and/or prevented; and "antiviral" refers to control of viruses such that the viral population is reduced, eliminated and/or prevented.

It is to be understood that both the foregoing general description and the following detailed description are exemplary and explanatory only and are intended to provide a further explanation of the present invention, as claimed.

The accompanying figures, which are incorporated in and constitute a part of this application, illustrate various features of the present invention and, together with the description, serve to explain the principles of the present invention. The features depicted in the figures are not necessarily drawn to scale. Similarly numbered elements in different figures represent similar components unless indicated otherwise.

DETAILED DESCRIPTION OF THE INVENTION

Figure 1:
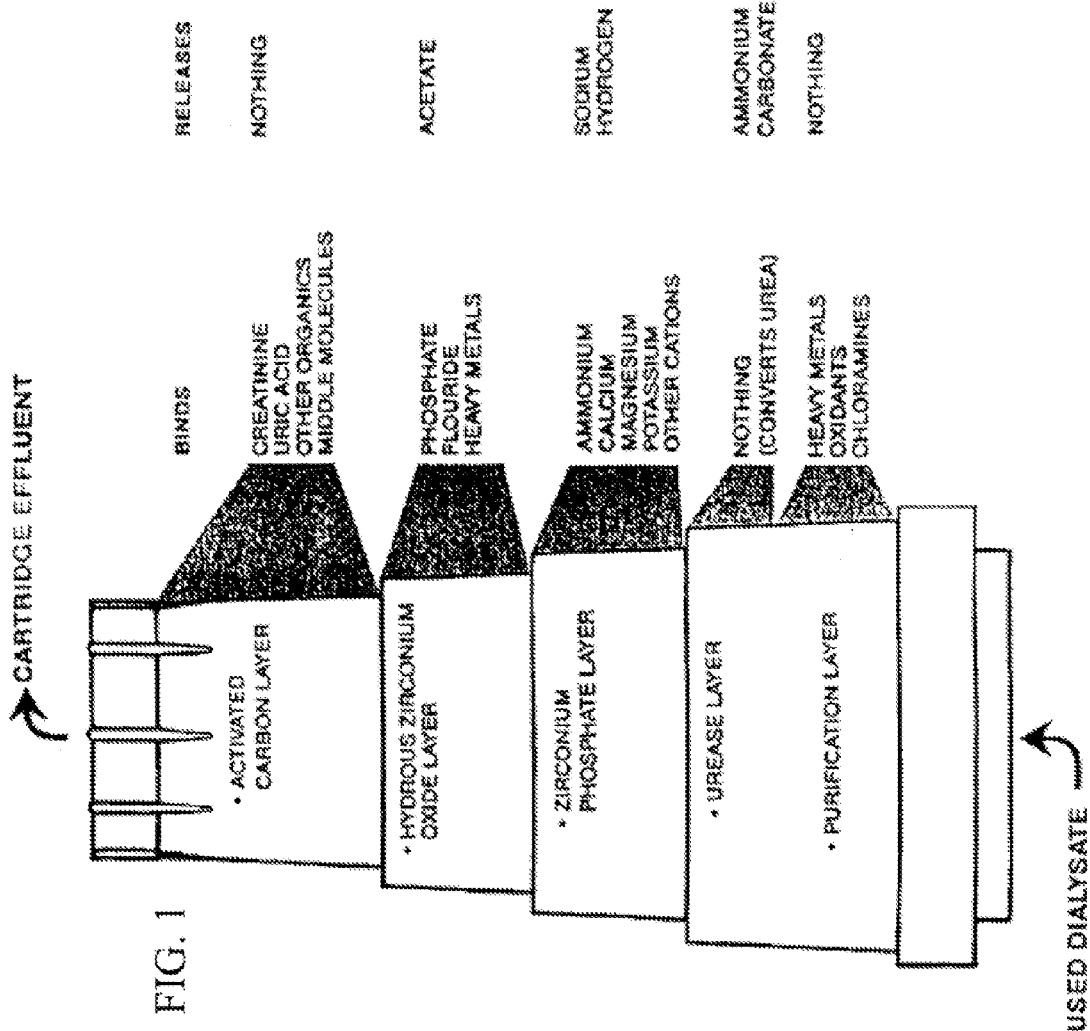
FIG. 1 is a diagram showing a cartridge and the various functions of each layer in a REDY® cartridge.
Figure 2:
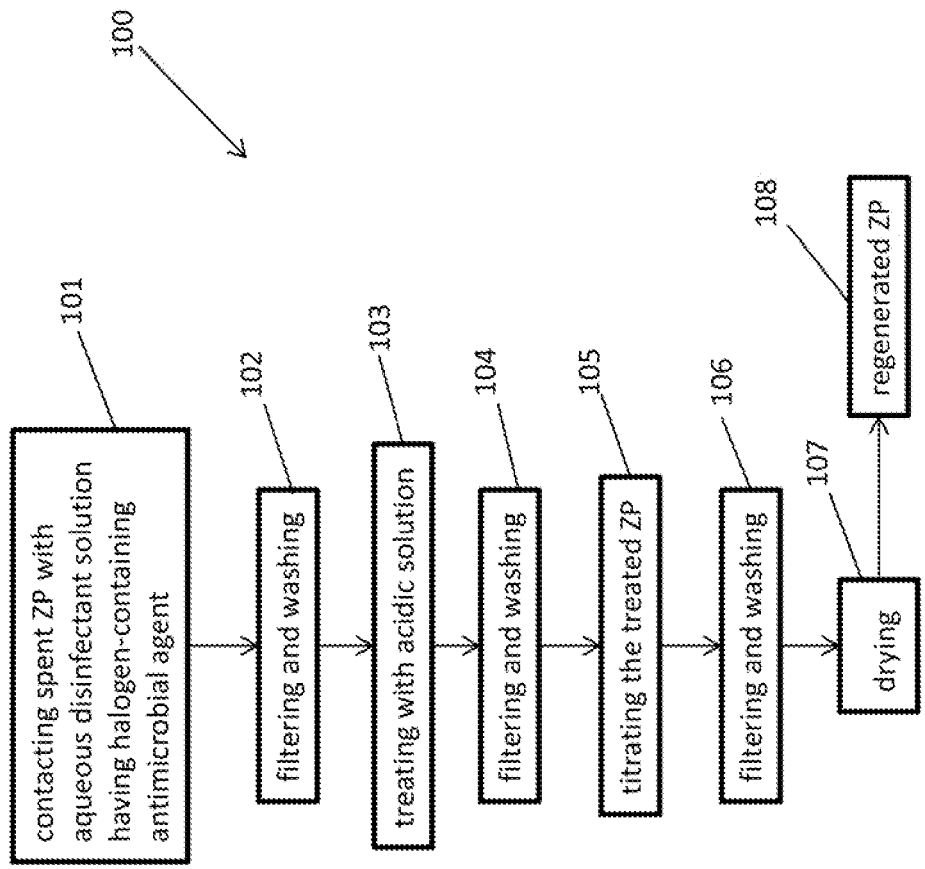
FIG. 2 is a process flow diagram showing a method according to an example of the present application.

The present invention relates to a method for regeneration of used or "spent" zirconium phosphate (ZP). In the method, spent zirconium phosphate can be disinfected with an aqueous disinfectant solution comprising at least one antimicrobial agent, and treated with an acidic solution to provide a treated zirconium phosphate. The resulting regenerated zirconium phosphate can have restored sorbent-related performance attributes substantially comparable to the virgin material, such as shown in the examples herein. The restoration can be sufficient that the resulting regenerated zirconium phosphate can be re-used as a sorbent material without adversely impacting performance in comparison to use of the virgin zirconium phosphate. For example, the spent zirconium phosphate that is regenerated in the present invention can be obtained from a sorbent cartridge that has been used in a sorbent-based dialysis treatment, and after regeneration, can be re-used in subsequent sorbent-based dialysis treatments or other kinds of sorbent treatments. By being able to regenerate sorbent zirconium materials from spent zirconium phosphate using a method of the present invention, the associated costs of acquiring or synthesizing fresh zirconium phosphate also can be reduced.

A method for regenerating spent zirconium phosphate of the present invention, for example, can comprise contacting spent zirconium phosphate with an aqueous disinfectant solution(s) comprising at least one antimicrobial agent to remove possible microbial contamination (e.g., bacterial contamination, fungal contamination, viral or combinations thereof) that has occurred during previous use in a sorption process, and then treating the disinfected zirconium phosphate with at least one acidic solution to remove cations adsorbed onto the material during the previous sorption process in which the zirconium phosphate was used. The type of disinfectant, and contacting time used for the disinfectant can be selected to be sufficient to control microorganisms that may be present in the spent zirconium phosphate. The acidic solution can comprise an acid that can strip or otherwise cause removal of at least one of the previously adsorbed metal ions from the spent zirconium phosphate wherein the metal ions can be transferred into the acid solution, rinsed off the sorbent material, or both. After the acid treatment, the treated zirconium phosphate can be neutralized. Titration can be applied, for example, to adjust a metal cation ($M^+$)/hydrogen ($H^+$) ionic balance on the treated zirconium phosphate material. For re-use in sorbent dialysis cartridge, for example, the indicated treated zirconium phosphate can be titrated to a target pH, wherein the relative content of sodium and hydrogen ions can be controlled by the pH to which zirconium phosphate is titrated. Filtering and washing can be used after any one or more (e.g., after all) of the indicated contacting step, treating step, and any titrating step. For example, the disinfected materials, acid treated materials, and titrated materials can be in a slurry form from which the aqueous fluid phase can be filtered or decanted off to isolate a wet cake containing the zirconium phosphate solids, which can be washed to remove unwanted impurities or residues, such as to preselected threshold values, before further processing. The treated (and titrated, if applicable) zirconium phosphate can be dried after a final washing step and before re-use. The dried regenerated zirconium phosphate can be in the form of a freely-flowable particulate material. Drying of the regenerated zirconium phosphate can facilitate handling, product stability, or have other purposes and effects. The regenerated zirconium phosphate also may be stored, handled, and/or re-used in other forms, such as slurry form (e.g., aqueous slurry form).

Sources of spent zirconium phosphate which can be regenerated with a method of the present invention can include, for example, zirconium phosphate used as sorbent material. The sorbent material can be a material that has been used in a sorption process such as adsorption, ion exchange, or chromatography. These sorption processes may comprise processes wherein certain adsorbates are selectively transferred from the fluid phase to the surface of insoluble zirconium phosphate particles packed in a cartridge or column, or suspended in a vessel. Spent zirconium phosphate for treatment can be obtained, for example, from sorbent dialysis cartridges, water purification/filtration cartridges, chromatography column packing materials, or other sources thereof. The spent zirconium phosphate can originate from virgin zirconium phosphate made by various synthesis methods, for example, such as those shown in U.S. Pat. No. 7,033,498, or U.S. Patent Application Publication No. 2010/084330, which are incorporated in their entirety by reference herein, or other synthesis methods. The size of the spent zirconium phosphate to which a regeneration method of the present invention is applied can be, for example, from an average particle size of from about 1 to about 150 microns or more, or from about 10 to about 100 microns, or from about 20 to about 75 microns, or other sizes. These particle sizes of starting spent materials can also apply to the zirconium phosphate particles after they have been regenerated by the method of the present invention.

As indicated, the zirconium phosphate regenerated from spent zirconium phosphate by a method of the present invention can be re-used as a sorbent material. The regenerated zirconium phosphate that is obtained by a method of the present invention can be used in the same type of process or device from which its spent form was obtained, or in a different type of process or device, or different portions thereof can be used in different types of processes or devices.

The present invention also relates to a sorbent cartridge comprising the indicated treated zirconium phosphate obtained by a method of the present invention. A dialysis system, for example, can be provided that comprises at least one dialyzer that uses dialysate to remove impurities from blood of a patient, and at least one of the indicated sorbent cartridges having the regenerated zirconium phosphate for regenerating the spent dialysate. A method to regenerate or purify spent dialysis fluid can comprise passing spent dialysis fluid through the indicated sorbent cartridge having the regenerated zirconium phosphate.

The regenerated zirconium phosphate obtained from spent zirconium phosphate by a method of the present invention can be used, for example, as the sole source of zirconium phosphate in a sorbent cartridge or as a blend with virgin zirconium phosphate in at least one component of a sorbent cartridge. For example, the regenerated zirconium phosphate can be used in place of at least a portion or all of virgin zirconium phosphate in at least one layer of a sorbent cartridge designed to include zirconium phosphate. As indicated, this can reduce or eliminate requirements for virgin zirconium phosphate and for disposal of spent zirconium phosphate from dialysis treatments or other sorbent treatments that use zirconium phosphate as sorbent material. At least one zirconium phosphate layer can be included in a sorbent cartridge, for example, that can comprise the indicated regenerated zirconium phosphate in a proportion of the total zirconium phosphate content thereof of at least about 1 wt. %, or at least about 5 wt. %, or at least about 10 wt. %, or at least about 20 wt. %, or at least about 25 wt. %, or at least about 30 wt. %, or at least about 40 wt. %, or at least about 50 wt. %, or at least about 60 wt. %, or at least about 70 wt. %, or at least about 75 wt. %, or at least about 80 wt. %, or at least about 90 wt. %, or at least about 95 wt. %, or at least about 99 wt. %, or more up to 100 wt. % content thereof, or from about 1 wt. % to about 100 wt. %, or from about 5 wt. % to about 99 wt. %, or from about 10 wt. % to about 90 wt. %, or from about 20 wt. % to about 80 wt. %, or from about 25 wt. % to about 75 wt. %, or from about 30 wt. % to about 70 wt. %, or other values. These indicated proportions of the regenerated zirconium phosphate also can apply to the total zirconium phosphate content of a sorbent cartridge.

In FIG. 1, a flow diagram shows a process for regeneration of spent zirconium phosphate according to an example of the present application. Process 100 includes steps 101 to 107, which are used to produce regenerated zirconium phosphate (ZP) from spent ZP. In step 101, spent zirconium phosphate is contacted with an aqueous disinfectant solution. The aqueous disinfectant solution comprises at least one antimicrobial agent. In step 102, the disinfected zirconium phosphate is filtered and washed to provide washed disinfected zirconium phosphate. The washing can be managed to provide a level of the antimicrobial agent in wash effluent of the washing of no greater than a first preselected value as indicating an extent of removal of the agent from the wet zirconium phosphate. In step 103, the washed disinfected zirconium phosphate is treated with an acidic solution to remove cations adsorbed thereon to provide a treated zirconium phosphate. In step 104, the treated zirconium phosphate is filtered and washed to provide washed treated zirconium phosphate. In step 105, the washed treated zirconium phosphate is titrated to a pH to provide neutralized zirconium phosphate. In step 106, the titrated zirconium phosphate is filtered and washed. In step 107, the washed titrated zirconium phosphate is dried to provide dried regenerated zirconium phosphate (108).

In an example, the at least one antimicrobial agent contained in the disinfectant solution can be at least one halogen-containing antimicrobial agent. The antimicrobial agent(s) can be a chlorine-containing compound, a bromine-containing compound, a fluorine-containing compound, an iodine-containing compound, or any combinations thereof. Other examples of antimicrobial agents include, but are not limited to, an oxidant(s), ozone, a peroxide(s), an acid(s) such as citric acid or other organic acid(s) and/or inorganic acid(s). The acid used in the acidic solution (for treating the disinfected zirconium phosphate with an acidic solution to provide a treated zirconium phosphate) could possibly be used as part or all of the antimicrobial agent, if this acid has sufficient antimicrobial properties. One or more antimicrobial agents can be used. The antimicrobial agent(s) can be used in dilute or concentrated forms. In an example, the disinfectant solution can contain at least one antimicrobial agent in an amount of from about 1 wt % to about 99 wt. %, or from about 2 wt. % to about 90 wt. %, or from about 3 wt. % to about 75 wt. %, or from about 4 wt. % to about 50 wt. %, or from about 5 wt. % to about 40 wt. %, or from about 6 wt. % to about 30 wt. %, or from about 7 wt. % to about 25 wt. %, or from about 8 wt. % to about 20 wt. %, or from about 9 wt. % to about 15 wt. %, or other amounts (based on the total wt. of the disinfectant solution). The disinfectant solution can contain a carrier fluid or medium, such as deionized water. The ratio of the antimicrobial agent(s) (on a pure basis) used relative to the spent ZP treated with the disinfectant solution can be, for example, from about 5:1 to about 50:1, or from about 10:1 to about 30:1, or from about 15:1 to about 25:1, or about 20:1, or other ratios, on a weight antimicrobial agent/weight ZP basis. The antimicrobial agent(s), for example, can be used in dilute aqueous solution forms. In an example, the antimicrobial agent of the disinfectant solution can be a chlorine-containing compound. The antimicrobial agent can comprise a bleach material, such as a hypohalite salt. Examples of hypohalite salts that can be used include alkali metal hypochlorite, alkaline earth metal hypochlorite, or any combinations thereof. The antimicrobial agent can be an inorganic compound. The antimicrobial agent can be dissolved, dispersed, or emulsified in the aqueous disinfectant solution. The antimicrobial agent can have a potency and concentration in the disinfectant solution effective to control viable microorganisms, such as viable bacteria and/or other microorganisms, residing in the spent zirconium phosphate after contact therewith.

The aqueous disinfectant solution can eliminate, for example, at least about 10%, or at least about 20%, or at least about 30%, or at least about 40%, or at least about 50%, or at least about 60%, or at least about 70%, or at least about 80%, or at least about 90% or more, up to 100%, or from about 10% to 100%, or from about 20% to about 90%, or from about 30% to about 80%, or from about 40% to about 70%, or other amounts, of the original amount of microorganisms (by count) contained by the spent zirconium phosphate. These levels of reductions can be applied, for example, to all originally viable forms of microorganisms in the spent zirconium phosphate or only bacteria, or only fungi, or only viruses, or any combinations thereof. The reduction of microorganisms in the spent zirconium phosphate can be quantitatively determined by any number of well known techniques in the art (e.g., direct assay for specific contaminants, biocompatibility testing, or optical contaminant analysis such as black light testing (luminescence).

The acidic solution used to treat the disinfected spent zirconium phosphate can comprise an acid in a liquid carrier, such as an aqueous carrier (e.g., deionized water). One or more acids can be used. The acid can be an acid that can remove cations adsorbed on the spent zirconium phosphate and transfer them into the carrier of the acidic solution to be carried away with that fluid. The acid can be an inorganic acid and/or an organic acid. The acid can be used in dilute or concentrated forms. In an example, the acidic solution can contain acid in an amount of from about 1 wt % to about 99 wt. %, or from about 2 wt. % to about 90 wt. %, or from about 3 wt. % to about 75 wt. %, or from about 4 wt. % to about 50 wt. %, or from about 5 wt. % to about 40 wt. %, or from about 6 wt. % to about 30 wt. %, or from about 7 wt. % to about 25 wt. %, or from about 8 wt. % to about 20 wt. %, or from about 9 wt. % to about 15 wt. %, or other amounts. The acidic solution can contain a carrier fluid or medium, such as water. The ratio of the acid (on a pure basis) used relative to the spent ZP treated with the acidic solution can be, for example, from about 25:1 to about 750:1, or from about 50:1 to about 600:1, or from about 100:1 to about 500:1, or about 350:1, or other ratios, on a weight acid/weight ZP basis. The acid can be, for example, HCl, HBr, HF, HI, HClO, $HClO_3$, $HClO_4$, $HBrO_4$, $HNO_3$, $H_2SO4$, or any combinations thereof. In an example, the acidic solution comprises a mineral acid, such as HCl. The acid can be selected to have a cation-removing capability and concentration in the acidic solution effective for removing at least a portion of the cations adsorbed onto the spent zirconium phosphate. The spent zirconium phosphate, before acid treatment, can contain greater than about 0-120 mg total cations/g zirconium phosphate, and the treating of the disinfected zirconium phosphate with the acidic solution can provide a treated zirconium phosphate having a total cation content of no greater than about 0-5 mg/g zirconium phosphate, or other values. These cation content values may be applied with respect to the total sodium, magnesium, calcium, and potassium ions content of the spent zirconium phosphate. The acidic solution can remove, for example, at least about 10%, or at least about 20%, or at least about 30%, or at least about 40%, or at least about 50%, or at least about 60%, or at least about 70%, or at least about 80%, or at least about 90% or more up to 100%, or from about 10% to 100%, or from about 20% to about 90%, or from about 30% to about 80%, or from about 40% to about 70%, or other amounts, all by weight, of the original amount of cations adsorbed onto the spent zirconium phosphate. The reduction of adsorbed cations from the spent zirconium phosphate can be determined, for example, by comparing the original level and level after acid treatment in the spent zirconium phosphate. The adsorbed cation levels on the spent zirconium phosphate before acid stripping can be determined from the cation levels added to the acid solution and the theoretical cation loading capacity of the material.

After the acid treatment step, the treated zirconium phosphate can be neutralized, e.g., titrated with an alkaline sodium ion-containing solution to recover and adjust the sodium ($Na^+$)/hydrogen ($H^+$) ionic balance on the material. For re-use in sorbent dialysis cartridge, for example, the treated zirconium phosphate can be titrated to a target pH. The relative content of these ions can be controlled, for example, by the pH to which acid ZrP (or $H^+ZrP$) can be titrated with an alkaline solution, such as an aqueous NaOH solution. For sorbent dialysis cartridge uses, for example, the treated zirconium phosphate can be titrated to a pH of about 5.5 to about 8.5 to provide titrated or neutralized zirconium phosphate.

As indicated, the regenerated zirconium phosphate can be titrated ZP in the Na+ and/or H+ form. A mixture of Na+ and H+ can be present in the ZP. The titrated (or neutralized) regenerated zirconium phosphate, for example, can have one or more of the following characteristics:

H+ content of from about 1.4 to about 2.0 wt %;
$Na^+$ content of from about 4 to about 6 wt %;
$ZrO_2$ content of from about 34 to about 37 wt %;
$PO_4^-$ content of from about 41 to about 43 wt %; and
$H_2O$ content from about 14 to about 18 wt %, based on the weight of the zirconium phosphate.

Other content amounts for the various characteristics can be used.

The titrated or neutralized regenerated zirconium phosphate of the present invention can have an adsorption capacity for ammonia. The adsorption capacity of the regenerated ZP when exposed to ammonium-nitrogen ($NH_4$—N) can be, for example, approximately from about 10 mg $NH_4$—N/g ZP to about 50 mg or more $NH_4$—N/g ZP. For purposes of this invention, a "dialysate solution" means a solution that can be used in hemodialysis or peritoneal dialysis, and, for example, having a sodium chloride concentration of about 105 mEq, and a sodium bicarbonate concentration of about 35 mEq. The sodium concentration of the dialysate solution can affect the ZP ammonia capacity, and the ZP particles can have an ammonia capacity in pure water that is greater than the ammonia capacity in dialysate solution.

As indicated, the disinfected materials, the acid treated materials, and any titrated materials can be in a slurry form from which the aqueous fluid phase can be filtered or decanted off to isolate a wet cake containing the zirconium phosphate solids, which can be washed to remove unwanted impurities or residues, such as to preselected threshold values, before further processing. For example, the number of washings, volumes of each washing, or both can be controlled. The washing of the disinfected zirconium phosphate, for example, can comprise washing the disinfected zirconium phosphate with an aqueous solution, such as deionized water (DI water), to obtain a halogen ppm level of about 0 ppm in the wash effluent.

The drying of the washed, treated, or titrated zirconium phosphate to provide dried regenerated zirconium phosphate can be done in any convenient manner. For example, the wet cake of treated/titrated particles can be air dried at room temperature with or without a vacuum applied, oven dried, radiant lamp dried, or by using other drying or heating methods. As indicated, the regenerated zirconium phosphate may be obtained and re-used in other forms, such as slurry forms.

In an example of the method of the present invention, for example, the used or spent zirconium phosphate can be disinfected with a bleach solution (e.g., about 1 to about 25 wt. % bleach, about 0.5-10 wt. % chlorine content), and acid treated with an aqueous HCl solution (e.g., about 1 to about 25 wt % HCl). In a further example, the used or spent zirconium phosphate (ZP) recovered from a spent sorbent cartridge can be first treated with aqueous bleach solution (e.g., about 8-12 wt. % pure bleach or about 10 wt. % pure bleach, about 5-6 wt. % chlorine content) to remove possible microbial contamination. Next, the zirconium phosphate can be filtered and washed with water, such as deionized water, until the total chlorine level of the effluent reaches about 0 ppm (e.g., ≤about 3 ppm). The zirconium phosphate then can be treated with an aqueous HCl solution (e.g., about 9 wt. % to about 13 wt. % HCl or about 11 wt. % HCl) to strip the cations adsorbed onto the material from the previous dialysis treatment(s) in which the cartridge was used to purify and regenerate spent dialysate. The zirconium phosphate can be filtered and washed with water (e.g., DI water) until the TDS level of the effluent is less than or equal to about 1200 ppm. To return the zirconium phosphate to substantially the same quality of material used in sorbent cartridges for dialysis, for example, the zirconium phosphate can be titrated to a target pH of from about 5.5 to about 8.5 (e.g., about 5.5 to 7, or about 5.75 to 6.5, or about 5.75) with aqueous NaOH solution (e.g., about 40 to 60 wt. % NaOH, such as about 50% wt. % NaOH). The zirconium phosphate then can be filtered and washed with water (e.g., DI water) until the TDS of the wet cake is less than or equal to about 500 ppm. Then, the zirconium phosphate can be dried, such as to a moisture level of from about 14 wt. % to about 18 wt. %. The dried regenerated zirconium phosphate is ready for (re)-use.

Figure 3:
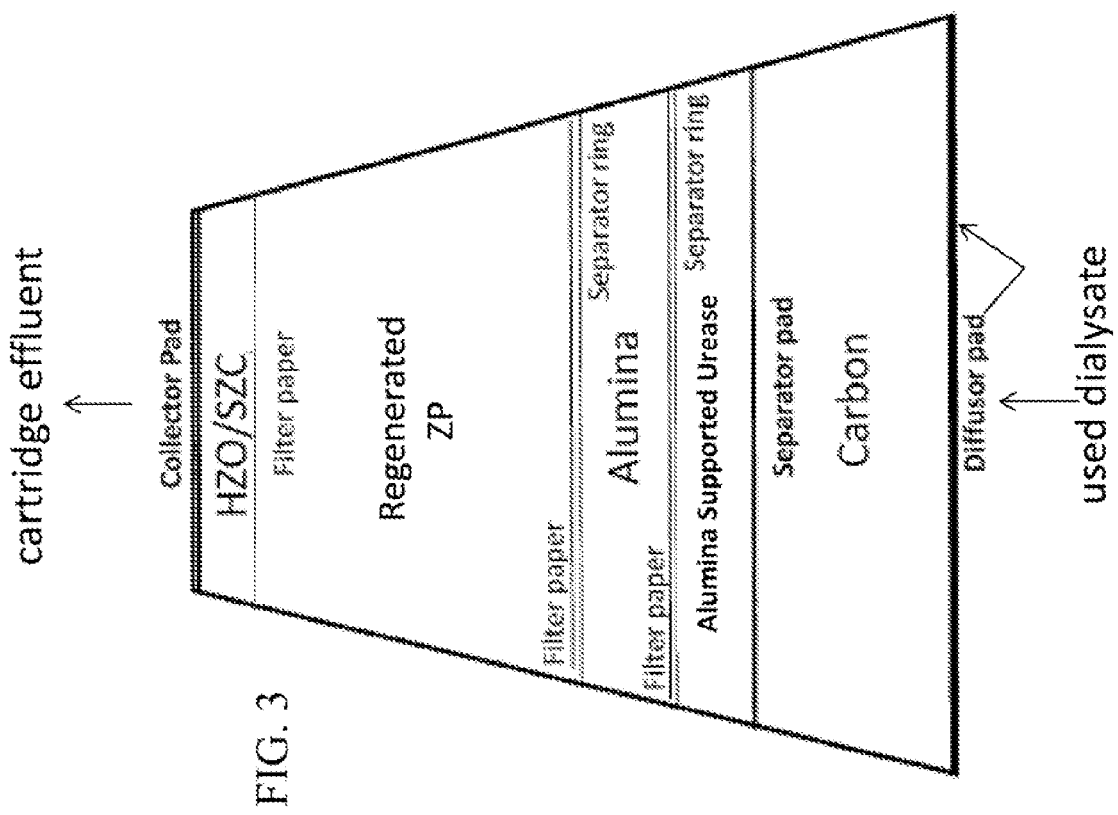
FIG. 3 is an exploded view of materials in a sorbent cartridge that contains regenerated zirconium phosphate according to an example of the present application.

FIG. 3 shows an example of sorbent cartridge design which can incorporate the regenerated zirconium phosphate of the present invention. FIG. 3 shows a sorbent cartridge and the direction of flow of used dialysate into and through the cartridge before discharged as effluent. The cartridge can include regenerated zirconium phosphate, a carbon layer, an alumina supported urease (e.g., immobilized Jack Bean meal), an alumina ($Al_2O_3$) backup layer, and a hydrous zirconium oxide/sodium zirconium carbonate layer ("HZO/SZC"), such as arranged in the sequence shown in FIG. 3. Additional features and components of the cartridge are illustrated, for example, in U.S. Pat. No. 7,033,498. The regenerated zirconium phosphate can be used in other sorbent cartridge designs, such as the REDY® cartridges or other sorbent cartridge designs that use zirconium phosphate.

Figure 4:
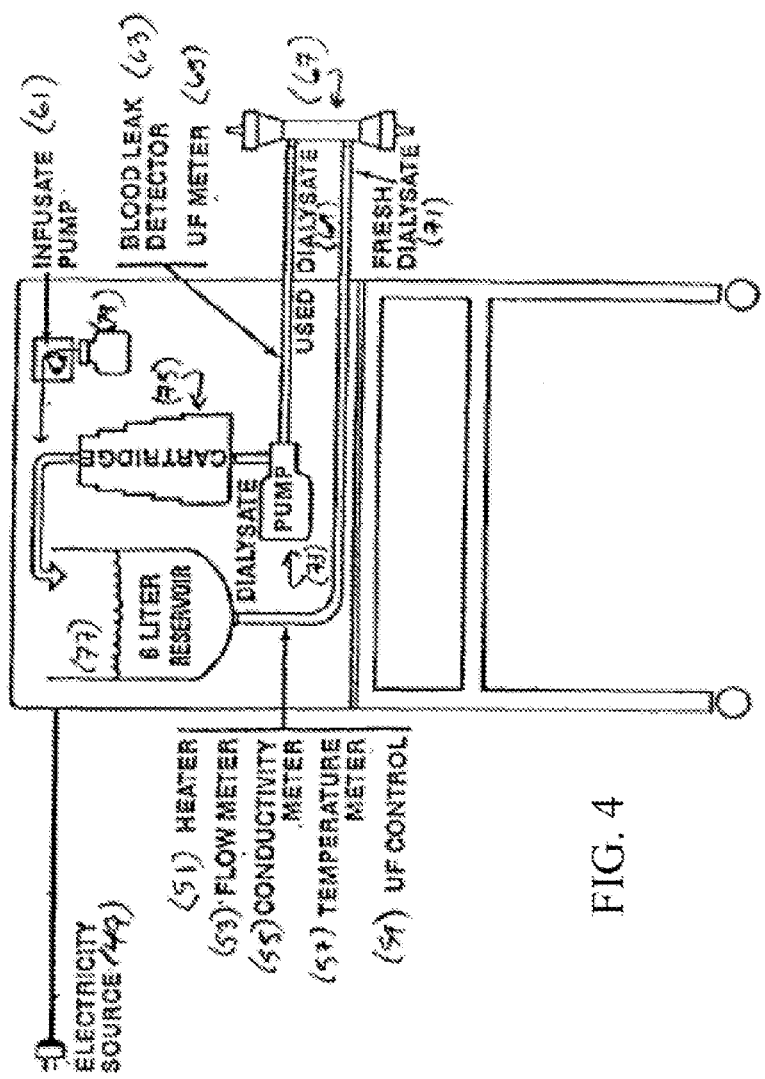
FIG. 4 is a schematic diagram showing a sorbent dialysis system which includes a sorbent cartridge according to an example of the present application.
Figure 5:
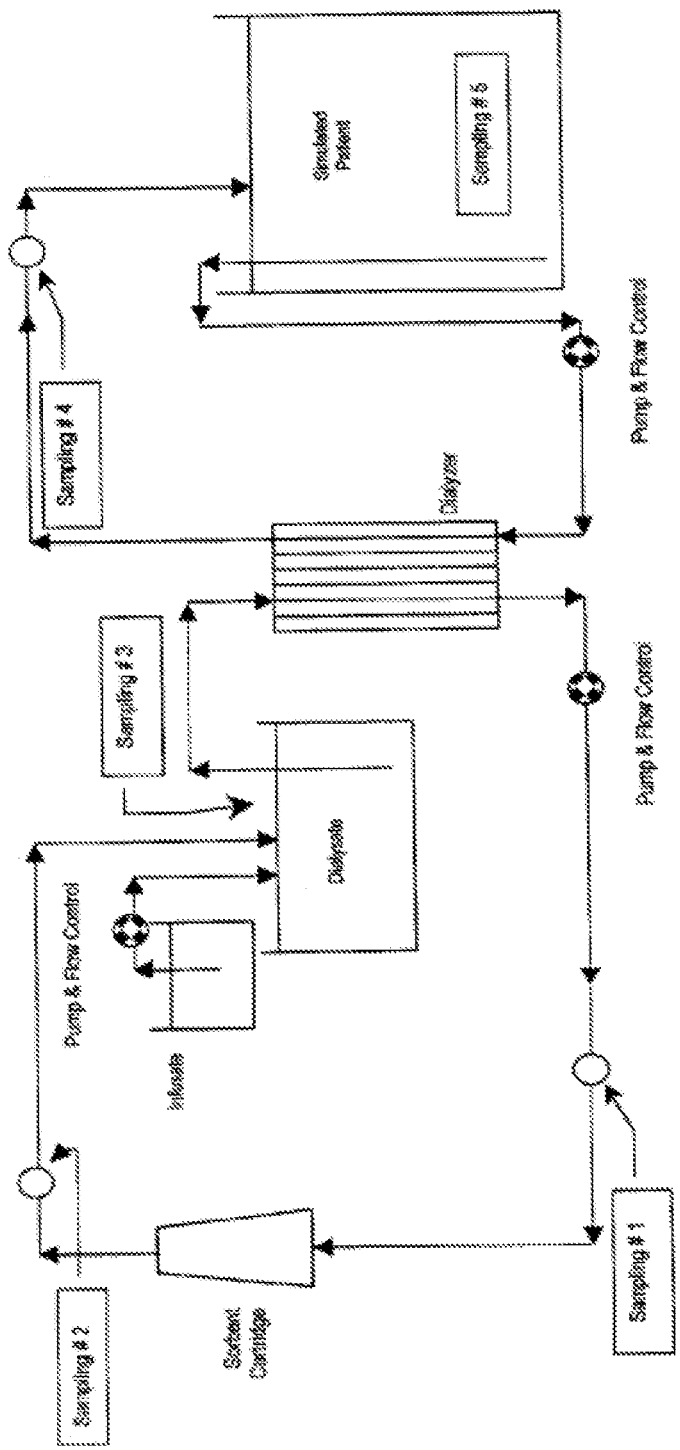
FIG. 5 is a schematic diagram showing a dialysis test set-up to test the sorbent cartridges according to an example of the present application.

Cartridges containing regenerated zirconium phosphate of the present invention, as indicated above, can be used in a variety of separation systems and can be used in the regeneration or purification of dialysates (e.g., hemodialysis (HD)) or peritoneal dialysis (PD) solutions. In a less complicated design, spent or used dialysate or PD solutions can simply be passed through one or more cartridges to purify or regenerate the spent fluids. Such a system can be straightforward in setup and can involve merely using a column-type setup wherein the spent fluids are passed from top to bottom wherein gravity permits the spent fluid to go through the cartridge or spent fluid can be passed through the cartridge under pressure which permits the spent fluids to be introduced in any direction, for instance as shown in FIG. 3. In a more specific system, the system set forth in FIG. 4 can be adapted to use an indicated sorbent cartridge as used especially for hemodialysis; that is a system that can be used as a closed system. The sorbent dialysis system shown in FIG. 4 can use a cartridge such as described above with respect to FIG. 3, or other designs that contain regenerated zirconium phosphate of the present invention, which is located as indicated in FIG. 4. Such a system permits the continuous reusing of the regenerated dialysate during a dialysis treatment.

With respect to peritoneal dialysis, there are several options. First, like hemodialysis, the peritoneal dialysis solution that is spent can be directly passed through one or more cartridges to purify or regenerate the used peritoneal dialysis solution in order to remove the waste products. Alternatively, the peritoneal dialysis solution which is used or spent can first be passed through a dialyzer in the same manner as blood during hemodialysis wherein dialysate removes waste products and the like from the peritoneal dialysis solution and then the dialysate can be regenerated or purified by passing the used or spent dialysate through the cartridge. Either system can be used in the present invention.

Referring to FIG. 4, 75 refers to a cartridge, which is a cartridge of the present application. 49 refers to a source of electricity to operate the dialysis system shown in FIG. 4. 51 represents a heater, 53 represents a flow meter, 55 represents a conductivity meter, 57 represents a temperature meter, and 59 represents a UF control. These items are conventional items in a sorbent dialysis system and are known to those skilled in the art and can be used in the present invention as shown in FIG. 4. 61 is an infusate pump that is used to pump in fresh concentrate 79 to be mixed with the regenerated dialysate which ultimately enters the reservoir 77 which can be a six liter reservoir. 63 represents a blood leak detector (when referring to a hemodialysis system) and 65 represents a UF meter which are conventional items in dialysis systems and can be used herein. Component 67 represents a dialyzer. As indicated, a dialyzer is known by those skilled in the art and typically is a component that includes a membrane through which waste products pass to the dialysate fluid. Similarly, 69 represents used dialysate leaving the dialyzer and 71 represents fresh dialysate entering the dialyzer 67. Component 73 is a pump for pumping the used dialysate from the dialyzer into the cartridge 75 which are the cartridges of the present application.

As indicated, sorbent cartridges fitted or retrofitted with regenerated zirconium phosphate of the present invention can provide performance in sorbent dialysis systems that is acceptable for typical treatments and can be substantially equivalent to cartridges using virgin zirconium phosphate material. For example, properties of a sorbent cartridge containing regenerated zirconium phosphate of the present invention at about 240 minutes usage can include at least one, two, three, four, five, six, seven, or eight, or all of the properties of:

i) $NH_3$—N leakage (mg %) of less than about 0.5,
ii) blood side urea nitrogen (BUN) leakage (mg %) of less than about 1.5,
iii) Na release of from about 140 to about 160 mEq/L,
iv) total $CO_2$ release of about 38 to about 46 mEq/L,
v) total Mg, Ca, and K leakage of less than about 0.2 mEq/L,
vi) pH of from about 6.8 to about 7.2,
vii) Ammonia Nitrogen Break-Through (ANBT) of from about 320 to about 350 minutes,
viii) Urea Nitrogen Capacity (UNC) of from about 38 to about 46 mEq/L, and/or
ix) maximum pressure of from about 14 to about 20 psi.

The present invention can be used with stationary sorbent dialysis systems or portable sorbent dialysis systems, which use sorbent cartridges containing regenerated zirconium phosphate. The sorbent dialysis systems can include sorbent hemodialysis, a wearable artificial kidney, sorbent peritoneal dialysis, and other sorbent dialysis systems.

The sorbent cartridges with regenerated zirconium phosphate of the present invention can be made for use in multiple hours of dialysis treatment, such as, for example, for up to about 4 hours of dialysis treatment or for up to about 8 hours of dialysis treatment. For example, the 8 hour cartridges can typically be made for home use and the 4 hour cartridges can typically be made for dialysis treatment in medical treatment or dialysis centers. The cartridges of the present invention can generally be used with any type of dialysis system as described above. The flows that pass through the cartridge are typically any conventional flows. For instance, flows from about 50 ml/min or less to 500 ml/min or more of dialysate can flow through the cartridge and can be used in the systems of the present invention. Other flows can be used depending upon the size of the cartridge and the operating system.

The dialysis systems or components thereof described in the following patents can be used in combination with the indicated regenerated zirconium phosphate of the present invention and these systems can incorporate the materials and/or cartridges of the present invention: U.S. Pat. Nos. 7,033,498 and 8,114,288, U.S. Published Patent Application Nos. US 2009/0173682, US 2010/0140149, US 2010/0252490, US 2011/0315611, US 2010/011401, US 2009/0127193, US 2011/0017665. All of these patents/publications are incorporated in their entirety by reference herein and form a part of the present application.

There are numerous uses for the regenerated materials of the present invention and especially the cartridges of the present invention such as the regeneration of dialysis fluids as mentioned above. Furthermore, the cartridges can be used in any separation process which requires the removal of impurities or waste products from a fluid or other medium that is passable through the materials of the present invention. The present invention may be useful with respect to treating drug overdose patients or other patients which are in need or removing undesirable or dangerous contaminants in a person's blood stream. The regenerated zirconium phosphate also may be used as a packing material in a chromatography column (e.g., ion exchange HPLC).

Accordingly, the present invention provides useful embodiments that allow the regeneration of zirconium phosphate for re-use.

The present invention includes the following aspects/embodiments/features in any order and/or in any combination:

1. The present invention relates to a method for regeneration of spent zirconium phosphate comprising:
   a) contacting spent zirconium phosphate with an aqueous disinfectant solution comprising a at least one antimicrobial agent to provide disinfected zirconium phosphate, and
   b) treating the disinfected zirconium phosphate with an acidic solution to provide a treated zirconium phosphate.
2. The method of any preceding or following embodiment/feature/aspect, wherein the treating removes cations adsorbed on the disinfected zirconium phosphate.
3. The method of any preceding or following embodiment/feature/aspect, further comprising filtering and washing the disinfected zirconium phosphate to provide washed disinfected zirconium phosphate before the treating step b).
4. The method of any preceding or following embodiment/feature/aspect, wherein the washing of the disinfected zirconium phosphate comprises washing the disinfected zirconium phosphate with an aqueous solution to obtain a halogen ppm level of about 0 ppm in wash effluent.
5. The method of any preceding or following embodiment/feature/aspect, further comprising c) filtering and washing the treated zirconium phosphate to provide washed treated zirconium phosphate.
6. The method of any preceding or following embodiment/feature/aspect, further comprising d) titrating the washed treated zirconium phosphate to a pH of about 5.5 to about 8.5 to provide titrated (or neutralized) zirconium phosphate.
7. The method of any preceding or following embodiment/feature/aspect, further comprising e) filtering and washing the titrated zirconium phosphate to provide washed titrated zirconium phosphate.
8. The method of any preceding or following embodiment/feature/aspect, further comprising f) drying the washed titrated zirconium phosphate to provide dried regenerated zirconium phosphate.
9. The method of any preceding or following embodiment/feature/aspect, wherein the antimicrobial agent is a halogen-containing antimicrobial agent that comprises a chlorine-containing compound.
10. The method of any preceding or following embodiment/feature/aspect, wherein the antimicrobial agent comprises hypohalite salt.
11. The method of any preceding or following embodiment/feature/aspect, wherein the antimicrobial agent comprises alkali metal hypochlorite, alkaline earth metal hypochlorite, or any combinations thereof.
12. The method of any preceding or following embodiment/feature/aspect, wherein the acidic solution comprises HCl, HBr, HF, HI, HClO, $HClO_3$, $HClO_4$, $HBrO_4$, $HNO_3$, $H_2SO4$, or any combinations thereof.
13. The method of any preceding or following embodiment/feature/aspect, wherein the acidic solution comprises HCl.
14. The method of any preceding or following embodiment/feature/aspect, wherein the washing of the treated zirconium phosphate comprises washing the treated zirconium phosphate until wash effluent of the washing has a total dissolved solids (TDS) level of no greater than about 1200 ppm.

15. The method of any preceding or following embodiment/feature/aspect, wherein the washing of the titrated zirconium phosphate comprises washing the titrated zirconium phosphate until the washed titrated zirconium phosphate has a total dissolved solids (TDS) level of no greater than about 500 ppm.

16. The method of any preceding or following embodiment/feature/aspect, wherein the dried regenerated zirconium phosphate has a moisture level of from about 14% to about 18% by weight.

17. The method of any preceding or following embodiment/feature/aspect, wherein the dried regenerated zirconium phosphate comprises free-flowing particles thereof.

18. The present invention also relates to a method for regeneration of spent zirconium phosphate comprising:
a) contacting spent zirconium phosphate with an aqueous disinfectant solution comprising at least one antimicrobial agent to provide disinfected zirconium phosphate,
b) filtering and washing the disinfected zirconium phosphate to provide washed disinfected zirconium phosphate with the washing providing a level of the antimicrobial agent in wash effluent of the washing of no greater than a first preselected value,
c) treating the washed disinfected zirconium phosphate with an acidic solution to remove cations adsorbed thereon to provide a treated zirconium phosphate,
d) filtering and washing the treated zirconium phosphate to provide washed treated zirconium phosphate with the washing providing a first total dissolved solids (TDS) level in wash effluent of the washing of no greater than a second preselected value,
e) titrating the washed treated zirconium phosphate to a pH of about 5.5 to about 8.5 to provide titrated (or neutralized) zirconium phosphate,
f) filtering and washing the titrated zirconium phosphate to provide washed titrated zirconium phosphate having a second total dissolved solids (TDS) level of no greater than a third preselected value, and
g) drying the washed titrated zirconium phosphate to provide dried regenerated zirconium phosphate.

19. The present invention also relates to a sorbent cartridge comprising the treated zirconium phosphate obtained by the method of any preceding or following embodiment/feature/aspect.

20. The present invention also relates to a dialysis system comprising at least one dialyzer that uses dialysate to remove impurities from blood of a patient, and at least one sorbent cartridge of any preceding or following embodiment/feature/aspect for regenerating the dialysate.

21. The present invention also relates to a method to regenerate or purify spent dialysis fluid comprising passing spent dialysis fluid through the sorbent cartridge of any preceding or following embodiment/feature/aspect.

22. The method of any preceding or following embodiment/feature/aspect, wherein properties of the sorbent cartridge at 240 minutes usage include at least one (e.g. 1, 2, 3, 4, 5, 6, 7, 8, or all 9 properties) of the properties of:
i) $NH_3$—N leakage (mg %) of less than about 0.5,
ii) blood side urea nitrogen (BUN) leakage (mg %) of less than about 1.5,
iii) Na release of from about 140 to about 160 mEq/L,
iv) total $CO_2$ release of about 38 to about 46 mEq/L,
v) total Mg, Ca, and K leakage of less than about 0.2 mEq/L,
vi) pH of from about 6.8 to about 7.2,
vii) Ammonium Nitrogen Break-Through (ANBT) of from about 320 to about 350 minutes,
viii) urea nitrogen capacity (UNC) of from about 38 to about 46 mEq/L,
ix) maximum pressure of from about 14 to about 20 psi.

The present invention can include any combination of these various features or embodiments above and/or below as set forth in sentences and/or paragraphs. Any combination of disclosed features herein is considered part of the present invention and no limitation is intended with respect to combinable features.

The present invention will be further clarified by the following examples, which are intended to be only exemplary of the present invention. Unless indicated otherwise, all amounts, percentages, ratios and the like used herein are by weight.

EXAMPLES

Example 1

Spent zirconium phosphate (ZP) was recovered from HISORB+ cartridges after the sorbent cartridges had been used in a simulated dialysis treatment of about 3.5 to 4 hours.

The spent ZP was regenerated in separate batches. In the ZP regeneration process that was used, 18 liters of process water was added to a reaction vessel, and 2.6 kg of spent ZP was added with agitation. 2 liters of bleach (assayed at 5%-6%) was added to the ZP slurry, and the ZP slurry was agitated for 60 minutes. The ZP slurry was filtered, and the ZP wet cake was washed with 20 liter aliquots of process water until total chlorine level was 0 ppm. In a clean reaction vessel, 20 liters of 11% HCl solution was added, and the ZP wet cake was slowly added to the HCl solution with agitation. The acidic solution treated wet cake was agitated for 60 minutes, and then the agitation was stopped and the ZP was allowed to settle. The liquid was decanted from the slurry, and 20 liters of process water was added to the reaction vessel. The slurry was agitated for 10 minutes, and then the ZP slurry was filtered. The ZP wet cake was rinsed with 20 liter aliquots of process water until TDS of effluent was ≤1200 ppm. In a clean reaction vessel, 8 liters of process water was added, and ZP wet cake was recovered and process water was added with agitation. The ZP slurry was titrated with 50% NaOH to a target pH of 5.75. The titrated slurry was allowed to agitate for 30 minutes, and then the titrated slurry was filtered. The ZP wet cake was rinsed with 20 liters process water until the wet cake TDS was ≤500 ppm. The ZP wet cake was dried to a moisture level of 14%-18%.

Adsorption Capacity of Regenerated ZP Material: The performance of the regenerated ZP was evaluated by measuring its adsorption capacity, which can be quantitatively determined by any number of well-known techniques in the art. By way of example, a sample of regenerated ZP was shaken in a known volume of a specified concentration of ammonium-nitrogen solution for a set amount of time. After shaking, the resulting slurry was filtered. The filtrate was subsequently analyzed for residual ammonium-nitrogen. From there, the amount of ammonium-nitrogen (NH4-N) adsorbed was calculated. Table 1 shows the adsorption capacity of the regenerated ZP, processed as described above, compared against the adsorption capacity of virgin ZP. The adsorption capacity of the virgin ZP was determined as described above.

TABLE 1

| Material | Adsorption Capacity (NH4—N/g ZP) |
|---|---|
| Virgin zirconium phosphate | 16 mg |
| Regenerated zirconium phosphate | 16-17 mg |

Adsorption Capacity of Regenerated ZP in a Cartridge: The regenerated ZP was used in place of virgin ZP in the construction of a sorbent cartridge having a configuration as shown in FIG. 3. An ammonium-nitrogen solution was made with known concentration. The solution was circulated through the column until the ammonium-nitrogen in the column effluent is ≥2.0 mg %. The amount of ammonium-nitrogen adsorbed was then calculated. Table 2 shows the adsorption capacity of the regenerated ZP compared against the adsorption capacity of virgin ZP.

TABLE 2

| Material contained in Column | Adsorption Capacity (NH4—N) |
|---|---|
| Virgin zirconium phosphate | 40.4-43.5 g |
| Regenerated zirconium phosphate | 42.3-44.6 g |

Overall, the sorbent cartridges made with regenerated ZP performed as well or better than the cartridge made with virgin ZP. The ability to take used (spent) ZP and regenerate it by a method of the present invention to a quality of material that has the performance characteristics of virgin material was shown.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method for regeneration of spent zirconium phosphate comprising:
    a) contacting spent zirconium phosphate particles with an aqueous disinfectant solution comprising at least one antimicrobial agent to provide a slurry of disinfected zirconium phosphate;
    b) filtering off aqueous fluid phase from the slurry of disinfected zirconium phosphate to isolate a wet cake containing disinfected zirconium phosphate;
    c) washing the wet cake containing the disinfected zirconium phosphate to provide washed disinfected zirconium phosphate; and
    d) treating the washed disinfected zirconium phosphate with an acidic solution to provide a treated zirconium phosphate.

2. The method of claim 1, wherein the treating removes cations adsorbed on the disinfected zirconium phosphate.

3. The method of claim 1, wherein the washing of the wet cake containing the disinfected zirconium phosphate comprises washing the wet cake containing the disinfected zirconium phosphate with an aqueous solution to obtain a halogen ppm level of about 0 ppm in wash effluent.

4. The method of claim 1, further comprising:
    e) filtering the treated zirconium phosphate to isolate a wet cake containing the treated zirconium phosphate; and
    f) washing the wet cake containing the treated zirconium phosphate to provide washed treated zirconium phosphate, wherein said washing the washed treated zirconium phosphate is with an aqueous solution.

5. The method of claim 4, further comprising g) titrating the washed treated zirconium phosphate to a pH of about 5.5 to about 8.5 to provide titrated zirconium phosphate.

6. The method of claim 5, further comprising:
    h) filtering the titrated zirconium phosphate to isolate a wet cake containing the titrated zirconium phosphate; and
    i) washing the wet cake containing the titrated zirconium phosphate to provide washed titrated zirconium phosphate.

7. The method of claim 6, further comprising j) drying the washed titrated zirconium phosphate to provide dried regenerated zirconium phosphate.

8. The method of claim 4, wherein the washing of the wet cake containing the treated zirconium phosphate comprises washing the wet cake containing the treated zirconium phosphate until wash effluent of the washing has a total dissolved solids (TDS) level of no greater than about 1200 ppm.

9. The method of claim 6, wherein the washing of the wet cake containing the titrated zirconium phosphate comprises washing the wet cake containing the titrated zirconium phosphate until the washed titrated zirconium phosphate has a total dissolved solids (TDS) level of no greater than about 500 ppm.

10. The method of claim 7, wherein the dried regenerated zirconium phosphate has a moisture level of from about 14% to about 18% by weight.

11. The method of claim 7, wherein the dried regenerated zirconium phosphate comprises free-flowing particles thereof.

12. The method of claim 1, wherein the antimicrobial agent comprises a chlorine-containing compound.

13. The method of claim 1, wherein the antimicrobial agent comprises hypohalite salt.

14. The method of claim 1, wherein the antimicrobial agent comprises alkali metal hypochlorite, alkaline earth metal hypochlorite, or any combinations thereof.

15. The method of claim 1, wherein the acidic solution comprises HCl, HBr, HF, HI, HClO, $HClO_3$, $HClO_4$, $HBrO_4$, $HNO_3$, $H_2SO4$, or any combinations thereof.

16. The method of claim 1, wherein the acidic solution comprises HCl.

17. A method for regeneration of spent zirconium phosphate comprising:
    a) contacting spent zirconium phosphate particles with an aqueous disinfectant solution comprising at least one antimicrobial agent to provide a slurry of disinfected zirconium phosphate;
    b) filtering off aqueous fluid phase from the slurry to isolate a wet cake containing the disinfected zirconium phosphate; and c) washing the wet cake containing the disinfected zirconium phosphate to provide washed disinfected zirconium phosphate with the washing providing a level of the antimicrobial agent in wash effluent of the washing of no greater than a first preselected value;
d) treating the washed disinfected zirconium phosphate with an acidic solution to remove cations adsorbed thereon to provide a treated zirconium phosphate;
e) filtering the treated zirconium phosphate to isolate a wet cake containing the treated zirconium phosphate; and
f) washing the treated zirconium phosphate to provide washed treated zirconium phosphate with the washing providing a first total dissolved solids (TDS) level in wash effluent of the washing of no greater than a second preselected value;
g) titrating the washed treated zirconium phosphate to a pH of about 5.5 to about 8.5 to provide titrated zirconium phosphate;
h) filtering the titrated zirconium phosphate to isolate a wet cake containing the titrated zirconium phosphate; and
i) washing the titrated zirconium phosphate to provide washed titrated zirconium phosphate having a second total dissolved solids (TDS) level of no greater than a third preselected value; and
j) drying the washed titrated zirconium phosphate to provide dried regenerated zirconium phosphate.

\* \* \* \* \*